United States Patent [19]

Kuntz

[11] 4,087,452

[45] May 2, 1978

[54] PROCESS OF HYDROCYANATION OF UNSATURATED ORGANIC COMPOUNDS CONTAINING AT LEAST ONE ETHYLENIC DOUBLE BOND

[75] Inventor: Emile Kuntz, Lyon, France

[73] Assignee: Rhone-Poulenc Industries, Paris, France

[21] Appl. No.: 758,149

[22] Filed: Jan. 10, 1977

[30] Foreign Application Priority Data

Jan. 13, 1976 France .................................. 76 00691

[51] Int. Cl.$^2$ ........................................... C07C 120/02
[52] U.S. Cl. .................................. 260/464; 252/437; 260/465 C; 260/465.3
[58] Field of Search .................. 260/465.3, 465 C, 464

[56] References Cited

U.S. PATENT DOCUMENTS

| | | | |
|---|---|---|---|
| 3,496,210 | 2/1970 | Drinkard, Jr. et al. | 260/465.3 |
| 3,655,723 | 4/1972 | Drinkard, Jr. | 260/465.3 |
| 3,686,264 | 8/1972 | Albanese et al. | 260/465.3 |
| 3,778,462 | 12/1973 | Taylor | 260/465.3 |
| 3,850,973 | 11/1974 | Seidel et al. | 260/464 |
| 3,925,445 | 12/1975 | King et al. | 260/465 C X |

*Primary Examiner*—Joseph Paul Brust
*Attorney, Agent, or Firm*—Bacon & Thomas

[57] ABSTRACT

A process of hydrocyanation of unsaturated organic compounds, which contain at least one ethylenic double bond, comprising reacting these compounds with hydrogen cyanide in the presence of an aqueous solution of a sulfonated triarylphosphine compound preferably a water soluble salt of a mono- di- or trisulfonated triphenylphosphine which contains a transition metal compound, preferably a nickel compound. When the reaction is completed the resulting hydrocyanated compound and the catalytic solution can easily be separated and the latter be reused.

35 Claims, No Drawings

PROCESS OF HYDROCYANATION OF UNSATURATED ORGANIC COMPOUNDS CONTAINING AT LEAST ONE ETHYLENIC DOUBLE BOND

BACKGROUND OF THE INVENTION

The invention relates to a process of hydrocyanation of unsaturated organic compounds.

The French Pat. No. 2,069,411 discloses a process for an addition of hydrogen cyanide to olefins in the presence of a complex of zerovalent nickel. The catalysts may be represented by the formula $(M'R'_3)_3Ni$ wherein $M'$ represents phosphorus and $R'$ represents a substituted or unsubstituted aryl. The catalysts can be prepared in advance or may be formed in situ. In the latter case a divalent nickel compound having a ligand $M'R'_3$ and a reducing agent is used. The hydrocyanation reaction may be performed within or without a solvent. The solvent which is liquid at the reaction temperature and inert towards the components of the reaction mixture, is always an organic compound usually a hydrocarbon like benzene or styrene or a nitrile, like acetonitrile or benzonitrile, wherein the reacting olefin is completely dissolved. Very often the ligand may serve as a solvent. The reaction is performed without adding any water to the components of the reacting system.

One of the major inconveniences of this type of process resides in the difficulties which are encountered after the reaction in separating the hydrocyanated products from the catalytic solution, which usually includes several constituents (a nickel complex in excess of a phosphorus containing ligand and a cocatalyst, usually a Lewis acid) especially as far as reutilization of the latter is considered. This separation is difficult and incomplete. Especially a substantial loss in catalyst is noted as well as the presence of catalyst in the separated hydrocyanated products.

In an article by F. Joo and M. T. Beck (Reaction Kinetics and Catalysis Letters, Vol. 2, No. 3, 257–263 (1975) these authors described their work concerning the use of a catalytic solution, which is obtained by mixing an aqueous acid solution of an Ru(III) compound and diphenyl phosphino-benzene-m-sulfonic acid, for the hydrogenation of cetocarboxylic acids.

SUMMARY OF THE INVENTION

It is an object of the present invention to provide an improved process for the hydrocyanation of unsaturated organic compounds containing at least one ethylene double bond by reaction with hydrogen cyanide or a hydrogen cyanide donor compound.

It is a further object of this invention to provide a process of hydrocyanation by which a higher yield of the hydrocyanated end product in relation to the amount of used hydrogen cyanide can be achieved.

It is a further object of this invention to provide a process of hydrocyanation which is highly selective in forming linear end products, e.g., linear dinitriles from linear unsaturated mononitriles.

It is another object of this invention to provide a process of hydrocyanation which allows a simple and economic recovery of the hydrocyanated end product and which especially allows for an easy recovery of an end product free from catalytic impurities.

It is a further object of this invention to provide a process of hydrocyanation which permits an easy recovery of most of the catalyst compounds, especially a process which permits the recovery of most of the catalytic solution for reuse in a further hydrocyanation process.

It is a further object of this invention to provide a continuous process for the hydrocyanation of unsaturated compounds.

It is a further object of this invention to provide a catalytic solution suitable for hydrocyanation processes, which is free from any byproducts which may interfere with the reaction or with the recovery of the end products from this reaction.

It is still a further object of this invention to provide such a catalytic solution, which can easily be recovered from the reaction mixture for reuse, especially a catalytic solution which is suitable for reuse in a continuous hydrocyanation process.

In order to accomplish the foregoing objects according to the present invention there is provided a process for hydrocyanation of unsaturated organic compounds which comprise at least one ethylenic double bond comprising the step of reacting at least one unsaturated organic compound which contains at least one ethylenic double bond with a compound from the groups of hydrogen cyanide or a hydrogen cyanide donor compound, e.g., cyanohydrines or cyanides, in the presence of an aqueous solution of at least one phosphine of Formula I:

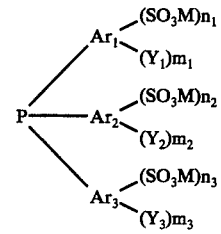

wherein $Ar_1$, $Ar_2$ and $Ar_3$ each represent an aryl group which may be alike or different from each other; $Y_1$; $Y_2$ and $Y_3$ which may be alike or different from each other each represent an alkyl group containing 1 to 4 carbon atoms, an alkoxy group containing 1 to 4 carbon atoms, a halogen, cyano-, nitro-, or hydroxy radical or an amino group

wherein $R_1$ and $R_2$ which may be alike or different from each other each represent an alkyl group containing 1 to 4 carbon atoms; -M represents any inorganic or organic cation which is able to form water soluble compounds of formula I, preferably a cation chosen from the group consisting of a proton, a cation derived from an alkaline metal or an alkaline earth metal or ammonium or a group $-N(R_3 R_4 R_5 R_6)^+$ wherein $R_3$, $R_4$, $R_5$ and $R_6$ each represent hydrogen or an alkyl group containing 1 to 4 carbon atoms and may be alike or different from each other, or a cation of any other metal which forms water soluble salts with benzosulfonic acids; $-m_1$ $m_2$ and $m_3$ each represent a whole number from 0 to 5 which may be the same or different from each other and $n_1$ $n_2$ and $n_3$ each represent an entire number from 0 to 3, which may be the same or different from each other, whereby at least one of these numbers $n_1, n_2$ and $n_3$ equals at least one, which further contains as a catalyst a compound of a transition metal. Preferably the transition metal compound is a nickel-palladium or iron compound most preferably a nickel compound and preferably at least part of the transition metal is zerovalent.

The process is preferably used for hydrocyanation of aliphatic or cyclic mono- or diolefines which are unsubstituted or substituted, e.g., substituted by a nitrile group.

When the hydrocyanating reaction is finished the cyanated product can easily be separated from the reaction mixture and a major portion of the catalytic aqueous solution can be recovered for reuse.

According to the present invention there is further provided a catalytic solution for hydrocyanation processes which comprises an aqueous solution of a phosphine of Formula I as defined above which contains a transition metal compound.

Further objects, features and advantages of the present invention will become apparent from the following detailed description of the invention.

DETAILED DESCRIPTION OF THE INVENTION

Further to the above-named cations M, cations which are derived from lead, zinc or tin can be cited as examples of cations which are able to form water soluble salts with benzosulfonic acids.

According to a preferred embodiment of the invention, the hydrocyanation process is performed in the presence of an aqueous solution containing such compounds of Formula I, wherein $Ar_1$, $Ar_2$, and $Ar_3$ each represent phenyl, $Y_1$, $Y_2$ and $Y_3$ which may be alike or different from each other, each represent an alkyl group containing 1 to 2 carbon atoms, an alkoxy group containing 1 to 2 carbon atoms or chlorine, M represents a proton, a cation derived from sodium, potassium, calcium or barium, ammonium, tetramethylammonium tetraethyl ammonium, tetrapropylammonium or tetrabutylammonium; $m_1 m_2$ and $m_3$ which may be alike or different from each other each represent a whole number between 0 and 3.

Among those phosphines of Formula I, the most preferred are the sodium, potassium calcium, barium, ammonium, tetramethylammonium and tetraethylammonium salts of (sulphophenyl)diphenylphosphine, di(sulfophenyl) phenylphosphine and tri(sulfophenyl)phosphine, wherein the $SO_3$- groups preferably are situated in meta position.

Further examples of phosphines of Formula I which may be used according to the process of the present invention are alkaline metal salts, alkaline earth metal salts, ammonium salts or quarternary ammonium salts of (m-sulfophenyl)diphenylphosphine, (p-sulfophenyl)diphenylphosphine, (m-sulfo-p-methylphenyl)di-(p-methylphenyl)phosphine, (m-sulfo-p-methoxyphenyl)-di(p-methoxyphenyl)phosphine, (m-sulfo-p-chlorophenyl)di(p-chlorophenyl)phosphine, di(m-sulfophenyl)phenylphosphine, di(p-sulfophenyl) phenylphosphine, di(m-sulfo-p-methylphenyl) (p-methylphenyl) phosphine, di(m-sulfo-p-methoxyphenyl) (p-methoxyphenyl)-phosphine, di(m-sulfo-p-chlorophenyl) (p-chlorophenyl)phosphine, tri(m-sulfophenyl) phosphine, tri(p-sulfophenyl) phosphine, tri(m-sulfo-p-methylphenyl)phosphine, tri(m-sulfo-p-methoxyphenyl)phosphine, tri(m-sulfo-p-chlorophenyl)phosphine, (o-sulfo-p-methylphenyl) (m-sulfo-p-methyl) phosphine, (o-sulfo-p-methylphenyl) (m-sulfo-p-methyl) phosphine, (m-sulfophenyl) (m-sulfo-p-chlorophenyl) (m,m'-disulfo-p-chlorophenyl)-phosphine.

As stated before, a mixture of these phosphines, particularly a mixture of mono- di- or tri-meta-sulfonated phosphines can be used.

As a transition metal compound preferably a nickel palladium or iron compound is used. Such compounds are used which are water soluble or able of being dissolved under the reaction conditions. The group which is connected to the transition metal is not critical as long as these requirements are fulfilled. Among the beforementioned compounds nickel compounds are most preferred. The following compounds are cited as non-limiting examples: compounds wherein the redox value of the nickel equals zero, such as potassium tetracyano nickelate $[K_4Ni(CN)_4]$ bisacrylonitrile nickel (zero), bis(cyclo-octadiene-1,5)$_2$ nickel and derivatives which contain ligands which include elements of the group VA, like tetrakis-(triphenylphosphine) nickel (zero). In this latter case the compound may be dissolved in a non-water miscible solvent like toluene from which an aqueous solution of a sulfonated phosphine extracts part of the nickel whereby a red coloration develops in the decantive aqueous solution, nickel compounds, e.g., nickel (II) compounds like nickel acetate, carbonate, carboxylate, bicarbonate, borate, bromide, chloride, citrate, thiocyanate, cyanide, formiate, hydroxides, hydrophosphite, phosphite, phosphate and its derivatives, iodide, nitrate, sulfate, sulfite, arylsulfonates and alkylsulfonates.

It is not necessary that the nickel compound as such is soluble in water. For example the nickel II cyanide is not very soluble in water but dissolves very well in an aqueous phosphine solution.

If in the used nickel compounds the oxydation value of the nickel is above zero, a nickel reducing agent, preferably a nickel reducing agent which reacts with the nickel under the given reaction conditions, is added to the reaction medium. This reducing agent may be an organic or inorganic agent. The following agents are cited as non-limiting examples: sodium borohydride, powdered zinc, magnesium potassium borohydride and other boron hydrides preferably water soluble boron hydrides.

It is advisable to add an amount of reducing agent which corresponds to between about 1 and about 10 redox equivalents. Nevertheless, the addition of lower amounts or higher amounts which correspond to more than 10 redox equivalents is not excluded. If the nickel compounds which are used contain zerovalent nickel, a reducing agent may also be added but this addition is not imperative. If iron compounds are used the same reducing agents are suitable. In the case of palladium, the components of the reaction medium (phosphine solvent, olefin) may also serve as reducing agents.

The sulfonated phosphines which are used within the process of the present invention can be prepared by conventional methods. Thus, according to the teachings of H. Schindlebauer, Monatsch. Chem. 96, pages 2051–2057 (1965) the sodium salt of (p-sulfophenyl)-diphenylphosphine can be prepared by reacting sodium p-chlorobenzene sulfonate with diphenylchlorophosphine in the presence of sodium or potassium. According to the method which is described in J. Chem. Soc., pp. 276–288 (1958) and in the British Pat. No. 1,066,261, phenylphosphines of Formula I can be prepared by using the method of sulfonating aromatic nuclei by means of oleum and then neutralizing the formed sulfonic groups by means of an appropriate basic derivative of one of the metals, which are represented by M in the Formula I. The crude sulfonated phosphines which are obtained may contain corresponding oxides of sulfonated phosphines mixed with them, yet the presence thereof does not interfere with performing the hydrocyanation process according to the present invention.

The process of the present invention is preferably suited for unsaturated organic compounds, which contain 2 to 20 carbon atoms and contain at least one ethylenic double bond. The following may be cited as examples: monoolefins such as ethylene, propylene, butene-1, 2-methylbutene-1, butene-2, pentene-1, pentene-2, hexene-1, 3-ethylhexene-1, 2-propylhexene-1, hexene-2, heptene-1, octene-1, octene-3, 4,4-dimethylnonene-1, decene-1, decene-2, 6-propyldecene-1, undecene-3, dodecene-1, tetradecene-5, 1′octadecene-1, 1′octadecene-2; cycloolefins such as cyclohexene and methylcyclohexenes substituted monoolefins such as pentene-4-nitrile, pentene-3-nitrile, styrene, 2-methylbutene-3-nitrile, methyl-styrene; diolefins such as butadiene, piperylene, isoprene, hexadiene-1,5, 1,4-cyclooctadiene.

The catalytic solution which is used for the hydrocyanation process according to this invention may be prepared in advance before it is introduced into the reaction zone, e.g., by adding an appropriate amount of the chosen transition metal compound and optionally a reducing agent to an aqueous solution of a phosphine of Formula I. It is also possible to prepare the catalytic solution in situ, e.g., by simply mixing the various components. The amount of the unsaturated compound which is added to the reaction mixture is not critical.

The amount of transition metal compounds especially nickel compounds which are used are chosen in such a range that the reaction solution contains between about $10^{-4}$ and about 1 gram atoms preferably between about 0.0005 and about 0.5 gram atoms of elementary metal per liter.

The amount of phosphine compounds of Formula I, which is used for preparing the reaction solution is chosen in a range that the reaction solution contains between about 0.5 and about 2000 preferably between about 2 and 300 moles of phosphines per gram atom of elementary metal.

Preferably, the reaction is performed at a pH value less than 12 preferably between 0 and 9. The appropriate pH value may be obtained by adding a pH modifying agent. These agents may be acids such as mineral acids and acidic compounds derived from elements of the group III A like boric acid, of the group IV A like carbonic acid, of the group V A like phosphoric acid and other acids derived from +5 valent or +3 valent phosphorus and arsenic acid, of group VI A like sulfuric acid, sulfurous acid and alkylsulfonic acids, of group VII like hydrofluoric, hydrobromic, hydrochloric and hydroiodic acids, or organic acids like trifluoromethane sulfonic acid, trifluoroacetic acid, arylsulfonic acids, alkulsulfonic acids, acetic acid or carboxyl acids, or bases such as hydroxides of alkaline metals or alkaline earth metals, ammonia, aliphatic or aromatic amines or a buffer solution corresponding to partially neutralized mixtures of the above cited acids and bases.

Although the reaction may be conducted starting from the present aqueous phosphine solution, it may be advantageous to add an inert organic solvent. There can be used a solvent which is immiscible with water and which may be the same which is used later for extraction or a solvent which is miscible with water, especially in cases of hydrocyanation of olefins which are not very soluble in water themselves.

The following are cited as examples of water miscible solvents: methanol, ethanol, propyl alcohol, isopropyl alcohol, acetone, acetonitrile, methyl ether, of diethylene glycol, and dimethoxyethane, and as examples immiscible solvents, benzene, benzonitrile, acetophenone, isopropyl ether, octane, methylethylacetone and propionitrile can be mentioned.

The temperature at which the reaction is performed may vary within wide ranges. Moderate temperatures of less than 200° C, preferably temperatures between about 20° and about 125° C are particularly suitable. Hydrogen cyanide donator compounds which may be used in the process of this invention are, for example, cyanhydrines and cyanides.

Hydrogen cyanide may be used in gaseous or liquid form or within a miscible or immiscible solvent or dissolved in the olefin which is to be hydrocyanated.

According to an embodiment of the process of this invention, an appropriate reaction vessel, which has been purged by means of an inert gas (nitrogen or argon) is charged either with an aqueous catalytic solution which was prepared before or with the various components, a phosphine solution in water, the transition metal compound optionally together with a reducing agent, a pH modifying agent and an organic solvent. The unsaturated organic compound is introduced. The reaction vessel is brought to the reaction temperature before or after the hydrogen cyanide is introduced, which itself may be introduced before, after or simultaneously with the unsaturated compound.

After stopping the reaction, the mixture is cooled to room temperature. The content of the reaction vessel is drawn from the vessel, and afterwards the reaction product has only to be recovered by subsequent decantation or eventually by extraction by means of appropriate solvents such as, e.g., the water immiscible solvents which were cited above.

The remaining aqueous solution may be recycled into the reaction vessel as a catalytic solution for a new operation of hydrocyanation. The process according to the present invention is especially well suited for continuous operation. The aqueous solution may also stay in the reaction vessel, when the organic compounds are drawn from it.

It was found that using an aqueous solution of a phosphine of the Formula I which contains a transition metal compound as a catalytic system allows to obtain yields of more than 80% in relation to the amount of hydrogen cyanides which were consumed.

It was also found that a high selectivity of the reaction, e.g., a selectivity of 92% can be achieved. This selectivity is expressed as the percentage of linear dinitrile which is present in the reaction product which is obtained from linear unsaturated starting materials such as pentene-3-nitrile.

Furthermore, the reaction speed was found to be high.

Another important advantage of the process according to the invention derives from the fact that the hydrocyanated products can easily be separated from the reaction mixture and the fact that the catalytic solution as such can be recycled to serve as a catalytic solution in another hydrocyanation reaction. In effect, the hydrocyanation products are simply decanted or extracted from the reaction mixture after the reaction is finished as was described above. Furthermore, the aqueous phase which contains the transition metal compound can be recycled without any loss of components of the catalytic system and consequently without any less of its activity.

The following examples are intended only to further illustrate the invention without limiting it.

EXAMPLE 1

(A) Preparation of the sodium salt of tri-(metasulfophenyl) phosphine.

Into a 2 liter balloon flask which is equipped with a central stirring system a thermometer and an ascendent cooler and which is cooled from the outside by a mixture of carbon dioxide (dry ice) and acetone there is introduced a liter of oleum containing 20% by weight of sulfuric anhydride, then the flask is purged with argon. The stirring is started, subsequently 100 g. of triphenylphosphine are introduced within 11 minutes, thereby keeping the temperature below 14° C. When the addition is finished stirring of the mixture is continued at room temperature between 20° and 26° C. during 62 hours. The reaction mixture is carefully poured into a 10 liter balloon flask which contains 2 liters of water and 4 kg of ice. This solution is neutralized by 6.2 kg octahydrated baryta which is added together with 4 liters of water at a temperature of 50° C. The precipitate is filtered and washed with water. The filtrate and the washing waters are united and concentrated to dryness. The obtained white product (A) is dried under vacuum at 0.1 mm of mercury and weighs 158 g. 141 g. of this product are dissolved in 2 liters of water and the solution is passed through a column which contains 1 liter of a strongly acid ion exchange resin (sulfonic acid) which is known under the tradename Amberlite IR 120, the resin is washed with water, the solution is concentrated to 500 ml and is neutralized with 58 ml of a 10 N sodium hydroxide solution. The solution is concentrated to dryness, the solids are washed with 1 liter of cold methanol and then 300 ml of methanol are added; the mixture is heated to boiling temperature and refluxed for 1 hour. After filtering and drying 53.2 g. of a white product (B) are obtained. The results of analyzing the solid product (B) by elementary analysis (determination of the content in C, H, S, P) by infra red spectroscopy by nuclear magnetic resonance of hydrogen and phosphorus and by chemical determination of the trivalent phosphorus and the sulfonated groups by ion exchange indicate that the product is a mixture of trisodium salts of tri(metasulfophenyl) phosphine (85%) and of tri(metasulfophenyl) phosphine oxide (15%).

The product A is the mixture of the barium salts corresponding to the mixture of sodium salts of product B. The composition of the mixture of salts may vary according to the temperature and the reaction time of the sulfonation. When the addition of the triphenylphosphine is effected at a temperature of about 30° C. and agitating of the mixture is continued at this temperature for about 20 hours, a mixture is recovered wherein 80% by weight of the salts in the solution are salts of tri(metasulfophenyl) phosphine. When working at 40° C. for 24 hours the obtained mixture of salts contains 60% by weight of the sodium salt of the tri(metasulfophenyl)phosphine. In these two latter cases the sodium salts are recovered by hydrolysis with sodium hydroxide and the sodium sulfate which is less soluble in water is partly removed by filtration and then completely removed by treating the residues which are obtained from the filtrate with methanol. The effluent of the ion exchange resin column contains the acid form of the sulfonated phosphine. The various salts may be prepared by neutralization with a base or a salt of a weak volatile acid which contains the appropriate cation.

(B) Preparation of an aqueous catalyst solution. Into a 10 ml flask which was purged with argon, 2.56 g. of the sodium salt of tri(meta-sulfophenyl)phosphine containing 85% of the pure salt, 0.148 g. of hexahydrated nickel II chloride and 3 ml of water are introduced. To this solution 1 ml of water containing 0.056 g. of sodium borohydride is added and a dark red colored solution is obtained. The flask is closed by means of rubber stopper through which a withdrawal by means of a syringe is possible.

(C) Hydrocyanation of pentene-3-nitrile.

Into a 10 ml glass tube [in the following examples the glass tube will be designated "tube (Ex. 1)"] which is filled with argon and is closed by means of a bakelite screw closure which comprises a rubber insert which allows the injection of liquids by means of syringe and which is provided with a rotating magnetic stirrer there are introduced successively 1 ml of the catalyst solution of paragraph B and 25 microliters of a solution of 9.3 moles/liter of hydrogen cyanide in ethanol (solution S). The tube is plunged into an oil bath, the temperature of which is maintained at 80° C. Now 0.5 ml of pentene-3-nitrile are introduced, 2 phases can be observed; a denser aqueous phase, which contains the catalyst and a supernatant organic phase, wherein the forming of adipic dinitrile (ADN) and methylglutaric dinitrile (MGN) are detected by chromatographic determination in withdrawn samples. During the testing more hydrogen cyanide solution (solution S) is added. The following table shows the addition conditions and the results, whereby the time of the introducing of the penetene-3-nitrile is taken as the starting time of the reaction.

TABLE

| Time in Minutes | Amount of Added Solution S in Microliters | Determination of dinitriles in the Supernatant phase | |
|---|---|---|---|
| | | ADN g/l | MGN g/l |
| 0 | — | 0 | 0 |
| 3 | — | 4.3 | 0.7 |
| 10 | — | 26 | 4.2 |
| 15 | — | 43 | 10 |
| 16 | 25 | — | — |
| 25 | — | 65 | 24 |
| 26 | 25 | — | — |
| 35 | — | 92 | 36 |
| 36 | 25 | — | — |
| 45 | — | 132 | 56 |

The supernatant phase contains the major part of the formed dinitriles; it does not contain any catalyst.

EXAMPLE 2

Into a tube (Ex. 1) 0.357 g. of the sodium salt of the tri(meta-sulfophenyl) phosphine containing 62% by weight of the pure salt, 1 ml of water, 0.02 g. of heptahydrated nickel sulfate, 0.0076 g. of sodium borohydride, 1 ml of styrene, 0.5 ml of ethanol and 16 microliters of a solution of 9.3 moles/liter of hydrogen cyanide in ethanol are introduced. The tube is plunged into an oil bath the temperature of which is maintained at 80° C. After a reaction period of 1½ hours the supernatant phase contains an amount of 1.5% phenyl-2-propionitrile relative to the amount of styrene. Now 16 microliters of the hydrogen cyanide solution are added and 15 minutes later another 50 microliters. One hour and 45 minutes after this addition the upper phase contains an amount of 5% phenyl-2-propionitrile relative to the amount of styrene, as is determined by vapor phase chromatography.

EXAMPLE 3

Instead of the styrene in Example 2, hexene-1 is used and the hydrocyanation is effected under the same conditions. When the operation is finished, the supernatant phase contains 3.3% of saturated mononitriles containing 7 carbon atoms.

EXAMPLE 4

Into 12.5 ml autoclave through which an argon stream is passed there are introduced 0.357 g. of the sodium salt of tri(metasulfophenyl)phosphine containing 62% by weight of the salt, 0.024 g. of heptahydrated nickel sulfate, 0.0076 g. of sodium borohydride and 0.5 ml of ethanol. The autoclave is cooled to −50° C., 2.5 ml of liquid butadiene and then 100 microliters of a solution of 9.3 moles/liter hydrogen cyanide in ethanol are introduced. The autoclave is closed, heated to a temperature of 80° C. and placed on a shaking machine for 4 hours. After cooling and degassing of the butadiene a reaction mixture consisting of 2 phases is recovered and is extracted 2 times with 5 ml of ether, a large portion of the ether is distilled off. By chromatographic determination it is found that the hydrogen cyanide is quantitatively transferred into ethylenic nitriles 81% of which is pentene-3-nitrile. Traces of unsaturated nitrile containing 9 carbon atoms are detected.

EXAMPLES 5, 6, 7, 8

(A) Preparation of an aqueous catalyst solution A:

Solution A

According to the method of Example 1 there is prepared a solution containing 5 ml of water.

5 millimoles of the crude sodium salt of tri(metasulfophenyl)phosphine containing 85% by weight of pure phosphine, 1.25 millimoles of hexahydrated nickel II chloride and 2.5 millimoles of sodium borohydride.

(B) Hydrocyanation of pentene-3-nitrile at room temperature:

Example 5

Into a tube (Ex. 1) are introduced 1 ml of the solution A, 0.5 ml of water and 0.5 ml of pentene-3-nitrile and then 15 microliters of a solution of 9.3 moles/liter of hydrogen cyanide in ethanol. After a reaction period of 80 minutes the supernatant solution contains 8.3 g./liter of adipic dinitrile and 0.7 g./liter of methylglutaric dinitrile. After 255 minutes it contains 18 g./liter of adipic dinitrile and 1.7 g./liter of methylglutaric dinitrile. The raito adipic dinitrile/methylglutaric dinitrile is above 10.

Examples 6, 7, 8

In 3 different tubes the 0.5 ml of water of Example 5 is replaced by 0.5 ml of 1 M sulfuric acid (Example 6) or 0.5 ml of a solution containing 0.25 moles/liter of $KH_2PO_4$ and 0.25 moles/liter of $Na_2HPO_4$ (Example 7), or 0.5 ml of a solution containing 2 moles/liter of sodium carbonate (Example 8), and the same amounts of catalytic solution and reactants as in Example 5 are added.

After a reaction period of 70 hours the supernatant solutions are analyzed and they contain:

|  | adipic dinitrile | methylglutaric dinitrile |
|---|---|---|
| Example 6 | 7.4 g/liter | 1.6 g/liter |
| Example 7 | 30.4 g/liter | 8.6 g/liter |
| Example 8 | 11.8 g/liter | 9.6 g/liter |

EXAMPLE 9

According to Example 1 a catalyst solution is prepared. Into a tube (Ex. 1) 1 ml of the catalytic solution, 0.5 ml of a solution which is prepared by mixing equal volumes of a solution containing 4.5 moles/liter of phosphorous acid and a solution containing 3 moles/liter of sodium hydroxide, and 25 microliters of an alcoholic solution of 9.3 moles/liter of hydrogen cyanide are introduced. The tube is plunged into an oil bath, the temperature of which is maintained at 80° C. When the temperature in the tube reaches 80° C., 0.5 ml of pentene-3-nitrile are added. After a reaction period of 2 minutes the supernatant solution contains 14.4 g/liter of adipic dinitrile and 1.15 g/liter of methylglutaric dinitrile. After a reaction period of 8 minutes the supernatant solution contains 21.8 g/liter of adipic dinitrile and 2 g/liter of methylglutaric dinitrile. While maintaining the temperature at 80° C. again 250 microliters of the solution of hydrogen cyanide and 0.2 g of sodium boron hydride are added in several portions. After a reaction period of 8 hours the supernatant solution contains 312 g/liter of adipic dinitrile and 160 g/liter of methylglutaric dinitrile.

EXAMPLE 10

In a tube (Ex. 1) there are introduced 0.49 g of the sodium salt of tri(metasulfophenyl)phosphine containing 85% by weight of the pure salt, 1 ml of water, 0.073 g of hexahydrated nickel II chloride and 0.010 g of zinc powder.

The tube is plunged into an oil bath, the temperature of which is maintained at 80° C. (time zero). When the temperature of the tube has reached 80° C., 0.5 ml of pentene-3-nitrile are added. Then after 20 minutes at 80° C. 2 times 30 microliters of a solution of 9.3 moles/liter of hydrogen cyanide in methanol are added at the following times: 35 minutes, 175 minutes and then 120 microliters at the time 230 minutes and then 120 microliters at the time 230 minutes. At the time 235 minutes the supernatant solution contains 8.5% adipic dinitrile and 8.1% methylglutaric dinitrile.

EXAMPLE 11

Into a tube (Ex. 1) there are introduced 0.49 g of the sodium salt of tri(metasulfophenyl) phosphine containing 85% by weight of the pure salt, 1 ml water, 0.073 g of hexahydrated nickel II chloride and 0.010 g of magnesium powder. The tube is plunged into an oil bath the temperature of which is maintained at 80° C. When the temperature of the tube has reached 80° C., 0.5 ml of pentene-3-nitrile are added. After a reaction period of 20 minutes the supernatant solution does not contain any dinitrile. Then hydrogen cyanide is added in the same way as in Example 9. After 235 minutes the supernatant solution contains 2.3% of adipic dinitrile and 2.7% of methylglutaric dinitrile.

EXAMPLE 12

Preparation of a water soluble nickel complex (A).

Into a 50 ml Schlenke tube there are introduced under argon 0.375 g of bis(cyclooctadiene-7.5) nickel and 5 ml of ethanol. Into an Erlenmeyer flask through which an argon stream is passed are introduced 3.30 g of the trisodium salt of tri(sulfophenyl)phosphine having a purity of above 95%, 17 ml of water and 25 ml of ethanol. The content of the Erlenmeyer flask is poured into the Schlenke tube, whereby a red color develops, and the mixture is agitated for 2 hours. The next day (15 hours later) the strongly colored solution is heated to boiling and is concentrated to dryness and the residue is dried under vacuum at 0.1 mm of mercury for 4 hours. The weight of the obtained product is 3.35 g and this product is tetrakis [trisodium salt of tri(metasulfophenyl)phosphine] nickel zero [elementary analysis; titration with iodine, a first turning point corresponding to the oxidation of nickel (disappearance of the color) and a second turning point corresponding to the oxidation of phosphine are determined. After neutralization of the iodic acid which is formed during the oxidation of the phosphine, a precipitation of nickel hydroxide in the basic medium is noted NMR studies (phosphorus 31) of the hydroalcoholic solutions at −40° C. demonstrates that large parts of the phosphine are part of a complex. NMR studies (phosphorus 31) of the aqueous solution of nickel II chloride and the phosphine (with a ratio phosphine/nickel equal to 6) and sodium borohydride (with a ratio boron/nickel equal to 2) at room temperature shows a quick exchange rate of ligands. By cooling to −40° C after addition of ethanol, the exchange rate of phosphines gets slow, 2 free phosphines per 4 phosphines which are part of a complex are observed].

Hydrocyanation of pentene-3-nitrile: Into a tube (Ex. 1) 1 ml of water and 0.276 g of the complex (A) are introduced. A clear intensely red solution is obtained. 16 microliters of a solution of 9.3 moles/liter of hydrogen cyanide in ethanol and then 0.5 ml of pentene-3-nitrile are added. After a reaction period of 4 hours at 24° C, the supernatant solution contains 6.8 g/liter of adipic dinitrile and 1.2 g/liter of methylglutaricdinitrile.

Preparation of the trisodium salt of tri(metasulfophenyl)phosphine having a purity of about 95%.

For the preparation of the complex, it is desirable to prepare a pure phosphine. The same components as in Example 7 (A) are used, but the sulfonation is effected at a temperature between 18° and 20° C during 48 hours. The reaction mixture is then hydrolyzed by means of 4 kg. of ice. The solution is brought to a pH of 7 by addition of 3.98 liter of 10 N sodium hydroxide solution. 7.5 liter of a homogenous solution are obtained. The major part of the sodium sulfate is eliminated by adding 3 liters of methanol. The filtrate is concentrated to dryness and the resulting residue contains the phosphines and sodium sulfate (this raw product can be directly put into an aqueous solution for performing hydrocyanation reactions). The raw product is washed with 1 liter of methanol; when the filtrate is concentrated to dryness a first crop (63.4 g) of phosphines containing a mixture of di- and tri-sulfonated phosphines is obtained. The insoluble residue of the filtration is treated under heating with 4 times 2.2 liters of methanol containing 10% of water. When these new united filitrates are concentrated to dryness a second crop of 136.9 g is obtained. 134 g of this second crop are dispersed in 140 ml of distilled water, after agitation the filtrate is poured into 900 ml of acetone, the precipitate is filtered, and dried to constant weight in an oven at 80° C.; yield 58 g. This product is the trisodium salt of tri(methasulfophenyl) phosphine of a purity of above 95%. The addition of an iodine solution to an aqueous solution leads to a quantitative formation of the trisodium salt of tri(metasulfophenyl)phosphine oxide and hydrogen iodide.

EXAMPLE 13

Into a tube (Ex. 1) 1 ml of water, 0.25 ml of ethanol, 0.4 millimole of the trisodium salt of tri(metasulfophenyl) phosphine of a purity of above 95% (see Example 12) and 0.1 millimole of bis(cyclooctadiene-1,5) nickel are introduced. The mixture is heated to 80° C. for half an hour and an intense red color appears. After cooling 16 microliter of a solution of 9.3 moles/liter of hydrogen cyanide in ethanol and then 0.5 ml of pentene-3-nitrile are added. The tube is plunged into an oil bath, the temperature of which is maintained at 80° C. After a reaction period of 30 minutes the supernatant phase contains 4.5 g/liter of adipic dinitrile and 2.6 g/liter and methylglutaric dinitrile.

EXAMPLE 14

An aqueous catalyst solution is prepared according to Example 1.

Into a tube (Ex. 1) 1 ml of the aqueous catalyst solution, 0.5 ml of benzene, 25 microliters of a solution of 9.3 moles/liter of hydrogen cyanide in ethanol and 0.5 ml of pentene-3-nitrile are introduced. The tube is plunged into an oil bath the temperature of which is maintained at 80° C. After a reaction period of 1 hour the supernatant solution contains 31 g/liter of adipic dinitrile and 10 g/liter of methylglutaric dinitrile.

EXAMPLE 15

Preparation of a disodium salt of di(meta-sulfophenyl) phenylphosphine and a trisodium salt of tri(-metasulfophenyl) phosphine of a purity of 95%.

These two sulfonated phenylphosphines are separately isolated from the reaction product of the following reaction: Into a 0.5 liter balloon flask which is equipped with a central stirring system, a thermometer and an ascendant cooler and which is cooled from the outside by a water/ice bath there are introduced 100 ml of oleum containing 20% by weight of sulfuric anhydride, then the flask is purged with argon. The agitation is started and then 10 g of triphenylphosphine ae introduced slowly whereby the reaction temperature is kept at 25° C. Agitation is continued at this temperature during 17 hours. The reaction mixture is then introduced into a recipient which contains 1000 g of ice and then neutralized by means of 400 ml of an aqueous solution of 10 N sodium hydroxide. The salts, which have precipitated are filtered and then dried to constant weight. The resulting solids which weigh 18 g are introduced into 65 ml of water which is heated to boiling temperature. By hot filtration the insoluble particles are eliminated and the filtrate is allowed to cool to 20° C. The solids which have precipitated are separated by filtration washed with 10 ml of cold water and then dried at 25° C. under vacuum at 0.1 mm of mercury during 30 hours. Thus, 8 g of pure disodium salt of di(metasulfophenyl) phenylphosphine are recovered.

The following analyses were effected for identifying this product: elementary analysis, infrared spectroscopy, nuclear magnetic resonance, determination of the trivalent phosphorus by iodometry. The filtrate which has been obtained from the filtration of the reaction mixture after the neutralization by means of sodium hydroxide is evaporated to dryness by heating under reduced pressure. 2000 ml of absolute ethanol are added to the obtained solids and the mixture is heated to 80° C., insoluble particles are eliminated by hot filtration and the filtrate is concentrated to a volume of 15 ml by evaporation. 200 ml of cold absolute ethanol are added and the precipitate which is formed is filtered, washed with ethanol and then dried at 25° C. under vacuum at 0.1 mm of mercury during 30 hours. Thus, 6.8 g of a trisodium salt of tri(metasulfophenyl)phosphine containing 95% by weight of the pure salt the remainder being the sodium salt of tri(metasulfophenyl)phosphine oxide. Hydrocyanation of pentene-3-nitrile. Into a tube (Ex. 1) 0.220 g of the disodium salt of di(metasulfophenyl) phenylphosphine, 1 ml of water, 0.024 g of heptahydrated nickel sulfate 0.0076 g of sodium borohydride, 16 microliters of a solution of 9.3 moles/liter of hydrogen cyanide in ethanol and 0.5 ml of pentene-3-nitrile are introduced. The tube is plunged into an oil bath the temperature of which is maintained at 80° C. After a reaction period of 2 hours 100 microliters of the hydrogencyanide solution are added. 2 hours and 15 minutes after this second addition the supernatant solution contains 30 g/liter of adipic dinitrile and 11 g/liter of methylglutaric dinitrile.

EXAMPLE 16

Preparation of the salt of mono(metasulfophenyl) diphenylphosphine. This phosphine is prepared according to the preparation method, which is described by S. Ahrland, J. Chatt, N. R. Davies and A. A. Williams in J. Chem. Soc. 276-288 (1958).

Hydrocyanation of pentene-3-nitrile.

The hydrocyanation is effected as is described in the preceding example whereby the disodium salt of the di(metasulfophenyl) phenylphosphine is replaced by 0.180 g of the sodium salt of mono(metasulfophenyl) diphenylphosphine. After a reaction period of 1 hour at 80° C. the supernatant solution contains 15 g/liter of adipic dinitrile and 4 g/liter of methylglutaric dinitrile.

EXAMPLE 17

Into a tube (Ex. 1) 0.4 millimole of the trisodium salt of tri(metasulfophenyl)phosphine (purity 85%), 1 ml of water, 0.1 millimoles of palladium acetate, 16 microliters of a solution of 9.3 moles/liter of hydrogen cyanide in ethanol and 0.5 ml of pentene-3-nitrile are introduced. The tube is plunged into an oil bath the temperature of which is maintained at 80° C. After a reaction period of 55 minutes the supernatant solution contains 3.3 g/liter of adipic dinitrile and 5.9 g/liter of methylglutaric dinitrile.

EXAMPLES 18 and 19

The same components as in the preceding example are used but the palladium acetate is replaced by 0.1 millimole of heptahydrated iron II sulfate, followed by 0.2 millimoles of sodium borohydride (Example 18), or by 0.1 millimole hexahydrated cobalt II chloride followed by 0.2 millimoles of sodium borohydride (Example 19). After a reaction period of 15 hours at 80° C. the supernatant solutions contain: Example 18: 3.1 g/liter of adipic dinitrile and 1.9 g/liter of methylglutaric dinitrile. Example 19: traces of adipic dinitrile and methylglutaric dinitrile.

EXAMPLE 20

Into a tube (Ex. 1) 0.366 g of the barium salt of tri(metasulfophenyl)phosphine (85% purity, prepared according to Example 1), 1 ml of water, 0.029 g of hexahydrated nickel nitrate, 0.0076 g of sodium borohydride, 0.5 ml of pentene-3-nitrile and 66 microliters of a solution of 9.3 moles/liter of hydrogen cyanide in ethanol are introduced. The tube is plunged into an oil bath, the temperature of which is maintained at 80° C. After a reaction period of 5 hours the supernatant phase contains 40 g/liter of adipic dinitrile and 18 g/liter of methylglutaric dinitrile.

EXAMPLE 21

Into a tube (Ex. 1) 0.350 g of a sodium salt of tri(metasulfophenyl)phosphine containing 85% by weight of pure salt, 1 ml of water, 0.024 g of hexahydrated nickel II chloride, 0.010 g of sodium borohydride, 14 microliters of acetone cyanhydrine, and 0.5 ml of pentene-3-nitrile are introduced. The tube is plunged into an oil bath, the temperature of which is maintained at 80° C. After a reaction period of 1 hour the supernatant solution contains 40 g/liter of adipic dinitrile and 20 g/liter of methylglutaric dinitrile.

What is claimed is:

1. A process for hydrocyanation of unsaturated organic compounds which contain at least one ethylenic double bond comprising the step of reacting at least one unsaturated organic compound which contains at least one ethylenic double bond with a compound from the group of hydrogen cyanide and a hydrogen cyanide donator compound in the presence of an aqueous solution comprising at least one phosphine of Formula I

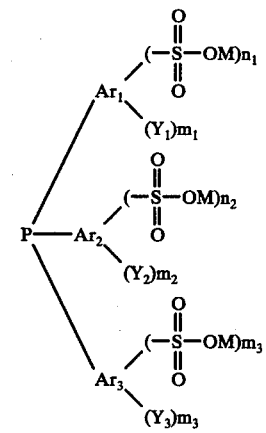

wherein $Ar_1$, $Ar_2$ and $Ar_3$ each represent an aryl group which may be alike or different from each other; $Y_1$, $Y_2$ and $Y_3$ which may be alike or different from each other each represent an alkyl group containing 1 to 4 carbon atoms, an alkoxy group containing 1 to 4 carbon atoms, a halogen, cyano-, nitro- or hydroxy radical or an amino group

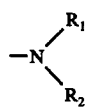

wherein R₁ and R₂ which may be alike or different from each other each represent an alkyl group containing 1 to 4 carbon atoms; M represents a cation which is able to form water soluble compounds of Formula I selected from the group consisting of a proton, a cation derived from an alkaline metal or an alkaline earth metal, ammonium, a group N(R₃R₄R₅R₆)+ wherein R₃, R₄, R₅ and R₆ each represent hydrogen or an alkyl group containing 1 to 4 carbon atoms and may be alike or different from each other, and a cation of any other metal, which is able to form water soluble salts with benzosulfonic acids; $m_1$, $m_2$, and $m_3$ each represent a whole number from 0 to 5 which may be the same or different from each other and $n_1$, $n_2$ and $n_3$ each represent a whole number from 0 to 3, which may be the same or different from each other, whereby at least one of these numbers $n_1$, $n_2$ and $n_3$ equals at least one and further comprising a compound of a transition metal and a nickel reducing agent when said transition metal compound is a nickel compound having an oxidation value of nickel above zero.

2. The process as defined in claim 1, wherein Ar₁, Ar₂ and Ar₃ each represent phenyl.

3. The process as defined in claim 1, wherein Y₁, Y₂ and Y₃, which may be alike or different from each other, each represent an alkyl group containing 1 to 2 carbon atoms, an alkoxy group containing 1 to 2 carbon atoms or chlorine.

4. The process as defined in claim 1, wherein M represents a proton, a cation derived from sodium, potassium, calcium or barium, ammonium, tetramethyl ammonium, tetraethyl ammonium, tetrapropyl ammonium or tetrabutyl ammonium.

5. The process as defined in claim 1, wherein $m_1$, $m_2$ and $m_3$ which may be alike or different from each other each represent a whole number between 0 and 3.

6. The process as defined in claim 1, wherein Ar₁, Ar₂ and Ar₃ each represent phenyl, Y₁, Y₂ and Y₃ which may be alike or different from each other, each represent an alkyl group containing 1 to 2 carbon atoms, an alkoxy group containing 1 to 2 carbon atoms or chlorine, M represents a cation of the group consisting of a proton, a cation derived from sodium, postassium, calcium or barium, ammonium, tetramethyl ammonium, tetraethyl ammonium, tetrapropyl ammonium or tetrabutyl ammonium and $m_1$, $m_2$ and $m_3$ which may be alike or different from each other each represent a whole number between 0 and 3.

7. The process as defined in claim 1, wherein Ar₁, Ar₂ and Ar₃ each represent phenyl, $n_1$ represents 1, $m_1$, $m_2$, $m_3$ each represent 0 and M represents a proton, a cation derived from sodium, potassium, calcium or barium, ammonium, tetramethyl ammonium or tetraethyl ammonium.

8. The process as defined in claim 1, wherein Ar₁, Ar₂ and Ar₃ each represent phenyl, $n_1$ and $n_2$ each represent 1, $m_1$, $m_2$, $m_3$ and $n_3$ each represent 0 and M represents a proton, a cation derived from sodium, potassium, calcium or barium, ammonium, tetramethyl ammonium or tetraethyl ammonium.

9. The process as defined in claim 1, wherein Ar₁, Ar₂ and Ar₃ each represent phenyl $n_1$, $n_2$ and $n_3$ each represent 1, $m_1$, $m_2$ and $m_3$ each represent 0 and M represents a proton, a cation derived from sodium, potassium, calcium or barium, ammonium, tetramethyl ammonium or tetraethyl ammonium.

10. The process as defined in claim 1, wherein said aqueous solution contains a mixture of at least two compounds of the Formula I wherein Ar₁, Ar₂ and Ar₃ each represents phenyl, $n_1$ represents 1, $n_2$ represents 0 or 1, $n_3$ represents 0 or 1, $m_1$, $m_2$ and $m_3$ each represent 0 and M represents a proton, a cation derived from sodium, potassium, calcium or barium, ammonium, tetramethyl ammonium or tetraethyl ammonium.

11. The process as defined in claim 5, wherein at least one of the sulfo groups which are present therein in each of the phenyl groups Ar₁, Ar₂ or Ar₃ is situated in m-position.

12. The process as defined in claim 1, wherein the transition metal is a metal from the group of nickel, palladium and iron.

13. The process as defined in claim 12, wherein the transition compound is nickel.

14. The process as defined in claim 12, wherein at least part of the transition metal is zerovalent.

15. The process as defined in claim 12, wherein the nickel compound is a compound from the group consisting of potassium tetracyano nickelate [K₄(CN)₄Ni], bis(acrylonitrile) nickel(zero), bis(cyclooctadiene-1,5)₂ nickel and tetrakis-(triphenylphosphine) nickel (zero).

16. The process as defined in claim 12, wherein the nickel compound is a compound from the group of nickel-acetate -carboxylate, -carbonate, -bicarbonate, -borate, -bromide, -chloride, -citrate, -thiocyanate, -cyanide, -formiate, -hydroxide, -hydrophosphite, -phosphite, -phosphate, -iodide, -nitrate, -sulfate, -sulfite, -arylsulfonates and -alkylsulfonates.

17. The process as defined in claim 12, which further comprises adding to the aqueous solution a reducing agent capable of reducing the transition metal.

18. The process as defined in claim 12, which further comprises adding a nickel reducing agent to the aqueous solution of the phosphine and the nickel compound.

19. The process as defined in claim 18, wherein the reducing agent is an agent from the group of sodium borohydride [BH₄Na], potassium borohydride, zinc powder, magnesium and water soluble boronhydrides.

20. The process as defined in claim 13, wherein the amount of nickel is from about $10^{-4}$ to about 1 gram atom per liter.

21. The process as defined in claim 20, wherein the amount of nickel is from 0.005 to about 0.5 gram atom per liter.

22. The process as defined in claim 12, wherein the amount of a phosphine of the Formula I is from about 0.5 to 2000 moles per gram atom of transition metal.

23. The process as defined in claim 22, wherein the amount of a phosphine of the Formula I is from about 2 to about 300 moles per gram atom of transition metal.

24. The process as defined in claim 1, wherein the reaction is performed at a pH valve between 0 and 12.

25. The process as defined in claim 1, which further comprises adding a pH adjusting agent to the aqueous solution.

26. The process as defined in claim 1, which further comprises adding an organic, water immiscible solvent to the aqueous solution.

27. The process as defined in claim 1, which further comprises adding an organic water miscible solvent to the aqueous solution.

28. The process as defined in claim 25, wherein the solvent is a solvent of the group of benzene, benzonitrile, acetophenone, ethyl ether, propyl ether, isopropyl ether, octane, methylethylketone and propionitrile.

29. The process as defined in claim 21, wherein the solvent is a solvent of the group of methyl alcohol, ethylalcohol, propylalcohol, isopropylalcohol, acetone, acetonitrile, methylether of diethylene glycol and dimethoxyethane.

30. The process as defined in claim 1, wherein the reaction is performed at a temperature less than about 200° C.

31. The process as defined in claim 17, wherein the amount of reducing agent is between about 1 to about 10 oxidation reduction equivalents.

32. The process as defined in claim 1, wherein the unsaturated organic compound contains 2 to 20 carbon atoms.

33. The process as defined in claim 1, wherein the unsaturated compound is a compound of the group of unsubstituted or substituted aliphatic or cyclic mono- or diolefins.

34. The process as defined in claim 1, which further comprises the step of recovering a hydrocyanated product and an aqueous solution containing the compound of Formula I and the transition metal compound.

35. The process as defined in claim 34, which further comprises recycling the recovered aqueous solution which is present at said reaction step.

* * * * *